United States Patent [19]
Niigata et al.

[11] Patent Number: 5,508,296
[45] Date of Patent: Apr. 16, 1996

[54] BISHETEROCYCLIC DERIVATIVE OR SALT THEREOF

[75] Inventors: Kunihiro Niigata, Saitama; Takumi Takahashi, Ibaraki; Takashi Yoneda, Chiba; Osamu Noshiro, Ibaraki; Reiko Koike, Ibaraki; Akiyoshi Shimaya, Ibaraki, all of Japan

[73] Assignee: Yamanouchi Pharmaceutical Co., Ltd., Tokyo, Japan

[21] Appl. No.: 190,093

[22] PCT Filed: Jul. 28, 1992

[86] PCT No.: PCT/JP92/00954

§ 371 Date: Jan. 31, 1994

§ 102(e) Date: Jan. 31, 1994

[87] PCT Pub. No.: WO93/03021

PCT Pub. Date: Feb. 18, 1993

[30] Foreign Application Priority Data

Jul. 30, 1991 [JP] Japan .................... 3-214326
Mar. 19, 1992 [JP] Japan .................... 4-093553

[51] Int. Cl.[6] ............ C07D 263/44; C07D 277/34; A61K 31/42; A61K 31/425
[52] U.S. Cl. ............ 514/369; 514/376; 548/183; 548/226
[58] Field of Search ............ 548/183, 226; 514/369, 376

[56] References Cited

U.S. PATENT DOCUMENTS 5,063,240  11/1991  Hindley .................... 514/369

FOREIGN PATENT DOCUMENTS 9200967  1/1992  WIPO.

*Primary Examiner*—Robert Gerstl
*Attorney, Agent, or Firm*—Burgess, Ryan and Wayne

[57] ABSTRACT

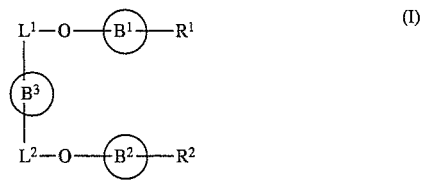

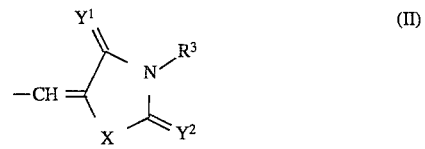

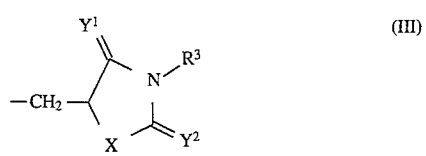

A bisheterocyclic compound represented by general formula (I), stereoisomers thereof, tautomers thereof, a pharmaceutically acceptable salt or a pharmaceutically acceptable solvate thereof, a pharmaceutical composition containing the same, and a process for the production thereof. In formula (I), $R^1$ and $R^2$ may be the same or different from each other and each represents (II) or (III), $R^3$ represents hydrogen or a protective group, X, $Y^1$ and $Y^2$ may be the same or different from one another and each represents oxygen or sulfur, $B^1$ and $B^2$ represent each phenylene, $B^3$ represents phenylene, naphthylene, cyclohexylene or furo[3,2-b]furanylene, $L^1$ and $L^2$ represent each $-(O)_n-A-$, n represents 0 or 1, and A represents a single bond or lower alkylene, provided that when n is 1, A represents alkylene and the oxygen atom of each of $L^1$ and $L^2$ is bonded to $B^3$. The above compounds are useful as a hypoglycemic drug based on the activity of enhancing insulin sensitivity.

9 Claims, No Drawings

BISHETEROCYCLIC DERIVATIVE OR SALT THEREOF

This application is a 371 of PCT/JP92/00945 filed Jul. 28, 1992.

TECHNICAL FIELD

This invention relates to a novel bisheterocyclic derivative which is useful a drug especially as a hypoglycemic drug, and to stereoisomers thereof, tautomers thereof, a pharmaceutically acceptable salt thereof, a pharmaceutically acceptable solvate thereof, a pharmaceutical composition containing the same and a process for the production thereof.

BACKGROUND ART

Synthetic hypoglycemic drugs currently used clinically as therapeutic agents for the treatment of diabetes are sulfonylurea preparations and biguanide preparations. Biguanide preparations, however, are used only in rare cases because of the limitation for their application due to their aptness to cause lactic acidosis. Sulfonylurea preparations, on the other hand, show solid hypoglycemic function and markedly small side effects, but must be used carefully because they sometimes cause hypoglycemia.

A number of studies have been made on the development of hypoglycemic drugs which can be used as substitutes for the sulfonylurea preparations, but with no success in putting them into practical use.

In recent years, insulin sensitivity enhancing agents which exhibit a hypoglycemic function by enhancing insulin sensitivity in peripheral tissues have received increased attention as substitutes for the aforementioned synthetic hypoglycemic drugs.

There are various compounds which have such an insulin sensitivity enhancing function, of which a thiazolidinedione compound disclosed in U.S. Pat. No. 5,063,240 and represented by the following formula is known as a bisheterocyclic type compound.

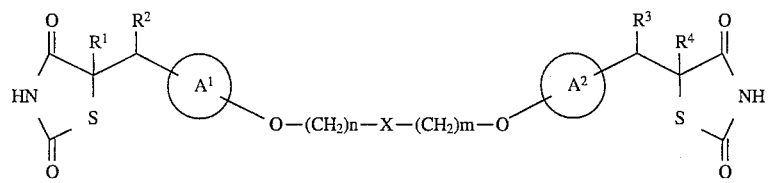

(See the above patent for the definition of each symbol in this formula.)

DISCLOSURE OF THE INVENTION

The inventors of the present invention have conducted screening of various compounds and found that a bisheterocyclic compound represented by the following general formula (I) whose structure is different from the compound disclosed in the aforementioned patent, as well as pharmaceutically acceptable salts and the like thereof, can show excellent hypoglycemic function based on the activity of enhancing insulin sensitivity and therefore can satisfy the clinical object. The present invention was accomplished based on this finding.

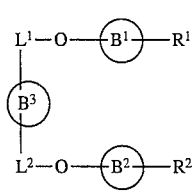 (I)

[In the above formula, $R^1$ and $R^2$ may be the same or different from each other and each represents a group of the formula:

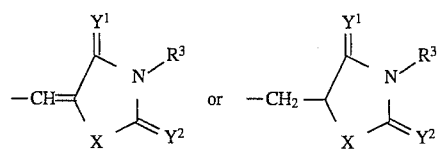

(wherein $R^3$ represents a hydrogen atom or a protective group and each of X, $Y^1$ and $Y^2$ represents a sulfur atom or an oxygen atom), each of $B^1$ and $B^2$ represents a phenylene group or a naphthylene group, $B^3$ represents a phenylene group, a naphthylene group, a cyclohexylene group or a furo[3,2-b]furanylene group represented by the following formula

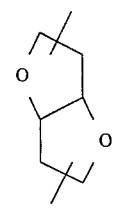

and each of $L^1$ and $L^2$ is a group represented by the formula $—(O)_n—A—$ (where A represents a single bond or a lower alkylene group and n is an integer of 0 or 1, provided that when n is 1, A represents a lower alkylene group and the oxygen atom of each of $L^1$ and $L^2$ is bonded to $B^3$).]

Accordingly, the present invention relates to a bisheterocyclic compound represented by the aforementioned general formula (I), stereoisomers thereof, tautomers thereof, a pharmaceutically acceptable salt thereof, a pharmaceutically acceptable solvate thereof, a pharmaceutical composition containing the same and a process for the production thereof.

In this instance, the compound of the present invention is characterized in that $B^3$ in the above general formula (I) is a phenylene group, a naphthylene group, a cyclohexylene group or a furo[3,2-b]furanylene group, and the inventive compound is therefore clearly different from the compound disclosed in the aforementioned patent in view of their structures. The following describes the compound of the present invention in detail.

In the compound (I) of the present invention, illustrative examples of the "phenylene group" represented by $B^1$, $B^2$ and $B^3$ include o-phenylene, m-phenylene and p-phenylene, and illustrative examples of the "naphthylene group" include 2,7-naphthylene, 2,6-naphthylene, 1,8-naphthylene, 1,5-naphthylene and the like.

Also, illustrative examples of the "cyclohexylene group" represented by $B^3$ include 1,2-cyclohexylene, 1,3-cyclohexylene and 1,4-cyclohexylene, and illustrative examples of the "furo[3,2-b]furanylene group" include 3,6-furo[3,2-b]furanylene, 2,5-furo[3,2-b]furanylene and the like.

In addition, the —A— moiety of the formula —(O)$_n$—A— represented by $L^1$ and $L^2$ is a single bond or lower alkylene, and this "lower alkylene" is an alkylene group having 1 to 6 carbon atoms, with its illustrative examples including methylene, ethylene, propylene (trimethylene), butylene (tetramethylene), pentamethylene and hexamethylene. The lower alkylene group may be substituted with one or two lower alkyl groups. Examples of the substituted lower alkylene group include methylmethylene, methylethylene, methylpropylene, dimethylmethylene, propylmethylene, ethylmethylmethylene and the like.

With regard to the protective group represented by $R^3$, protective groups for acidic nitrogen which can be eliminated easily by reduction or with an acid may be used, with their preferred illustrative examples including trityl, benzhydryl, methoxycarbonyl, benzyloxycarbonyl, methoxybenzyl, p-nitrobenzyl and the like.

Since the compound (I) of the present invention has double bonds and asymmetric carbon atoms and contains carbonyl and thiocarbonyl groups, their presence results in the formation of stereoisomers such as geometrical and optical isomers and tautomers. All of these isomers, isolated or as a mixture, are included in the present invention.

Since a compound in which a thiazolidine ring or a oxazolidine ring has an acidic nitrogen is included in the compound (I) of the present invention, it can form a salt with a base. The present invention includes pharmaceutically acceptable salts of the compound (I), and examples of these salts include those with metals such as sodium, potassium, calcium, magnesium, aluminium and the like and those with organic bases such as methylamine, ethylamine, dimethylamine, diethylamine, trimethylamine, triethylamine, monoethanolamine, diethanolamine, triethanolamine, cyclohexylamine, amino acids such as lysine and ornithine and the like.

The present invention also includes pharmaceutically acceptable various solvates, such as hydrates, of the compound (I), as well as polymorphic forms thereof.

Particularly preferred among the inventive compounds represented by the aforementioned general formula (I) is a compound in which $R^1$ and $R^2$ are

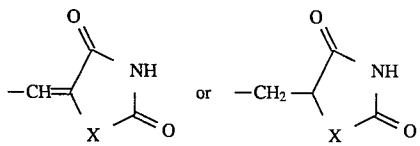

and $B^3$ is a phenylene group or a cyclohexylene group.

Typical examples of the compound of the present invention are as follows.

Trans-1,4-bis[[4-[(2,4-dioxo-5-thiazolidinyl)methyl]phenoxy]methyl]cyclohexane

Trans-1,4-bis[[4-[(2,4-dioxo-5-oxazolidinylidene)methyl] phenoxy]methyl]cyclohexane Trans-1,4-bis[[4-[(2,4-dioxo-5-oxazolidinyl)methyl]phenoxy]methyl]cyclohexane 1,3-Bis[4-[(2,4-dioxo-5-oxazolidinyl)methyl]phenoxy]benzene 1,3-Bis[4-[(2,4-dioxo-5-oxazolidinylidene)methyl]phenoxy]benzene 1,3-Bis[4-[(2,4-dioxo-5-oxazolidinyl)methyl]phenoxy]cyclohexane 1,3-Bis[4-[(2,4-dioxo-5-thiazolidinyl)methyl]phenoxy]cyclohexane The compound (I) of the present invention can be produced making use of various processes, by taking into consideration its chemical structure characteristics such as basic skeleton, substituent groups and the like. The following illustrates typical production processes. Production process 1

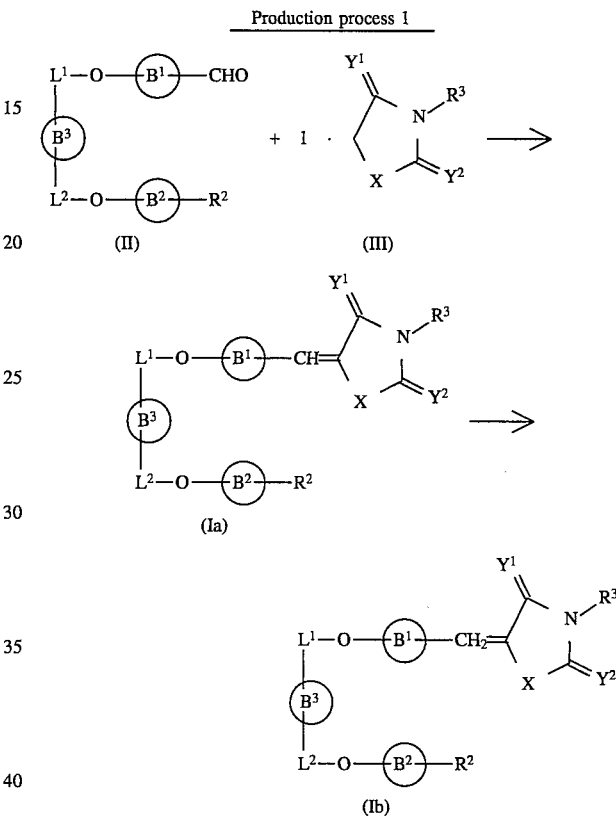

(In the above reaction formulae, each of $B^1$, $B^2$, $B^3$, $L^1$, $L^2$, X, $Y^1$, $Y^2$, $R^2$ and $R^3$ has the same meaning as described in the foregoing, and $R^a$ is a formyl group or a group represented by the aforementioned $R^2$. In addition, l is 2 when $R^a$ is a formyl group or 1 in other cases.)

The heterocyclic derivative represented by the general formula (Ia) is produced by a usual condensation reaction (Knoevenagel condensation) in which a mono- or bisaldehyde derivative represented by the general formula (II) is allowed to react with a thiazoline or oxazoline derivative represented by the formula (III).

Another heterocyclic derivative represented by the general formula (Ib) is produced by reducing the compound (Ia).

It is desirable to carry out the condensation reaction at room temperature or with heating, preferably with heating, using the compounds (II) and (III) in an approximately equal or two-fold mol basis, or either one in a slightly excess amount than its chemical equivalent, in an organic solvent including an alcohol such as ethanol, methanol or the like, tetrahydrofuran, diethyl ether, methylene chloride, chloroform, benzene, toluene, acetonitrile or the like, or in water or a mixture thereof, in the presence of an acetic acid-piperidine mixture, β-alanine, alumina, titanium tetrachloride, tin tetrachloride, boron tetrafluoride, potassium fluoride, sodium hydroxide, potassium hydroxide, sodium carbonate, ammonium acetate, an alkali metal alkoxide such as sodium ethoxide, potassium t-butoxide or the like or a base such as diethylamine, triethylamine, pentylamine, pyridine or the like.

The compound (Ib) of the present invention is produced by reduction of carbon-to-carbon double bond making use of, for example, a hydrogenation reaction with a catalyst such as a palladium on carbon or the like, or a reduction reaction with a metal hydride such as lithium borohydride, sodium borohydride or the like. The reduction reaction with a metal hydride may be carried out preferably using dimethylimidazolidinone as the solvent and sodium borohydride as the reducing agent at usually an elevated reaction temperature.

In this instance, an unsymmetric compound having different heterocyclic groups can be produced easily by allowing a starting compound (II) in which $R^a$ is $R^2$ to react with a starting compound (III) having a heterocyclic group which is different from the heterocyclic group of $R^2$.

Production process 2

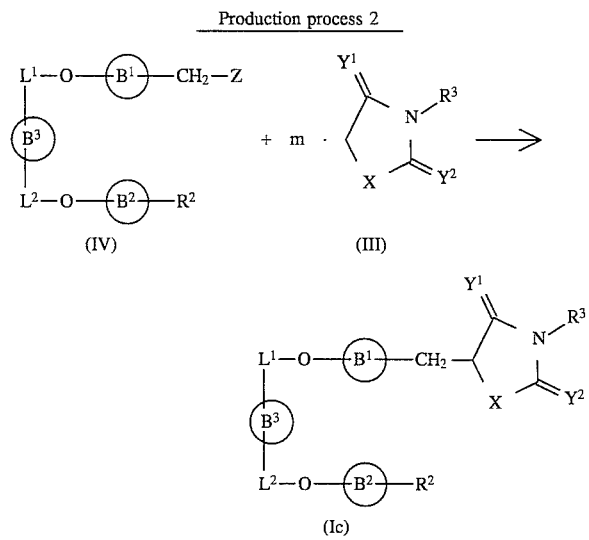

[In the above reaction formulae, each of $B^1$, $B^2$, $B^3$, $L^1$, $L^2$, X, $Y^1$, $Y^2$, $R^2$ and $R^3$ has the same meaning as described in the foregoing, Z represents a halogen atom, $R^b$ is a group represented by a formula —$CH_2$—Z (where Z has the just described meaning) or the group $R^2$ and m is 2 when $R^b$ is the group represented by the formula —$CH_2$—Z or 1 in other cases.]

The compound of the present invention represented by the general formula (Ic) is produced by allowing a mono- or bishalide represented by the general formula (IV) to react with an oxazolidine or thiazolidine compound represented by the general formula (III).

Examples of the halogen atoms include iodine, bromine, chlorine and the like.

It is advantageous to carry out the reaction by making the compound (III) into an active methylene compound, in the presence of a base such as n-butyl lithium, magnesium methylcarbonate, lithium diisopropylamide, potassium hexamethyldisilazide or the like, using the compound (III) in an approximately equal mol or two-fold mols based on the compound (IV), or either one in a slightly excess amount than its chemical equivalent, in an inert organic solvent such as ether, dimethyl ether, tetrahydrofuran, dioxane, dimethylformamide, an alcohol such as methanol, ethanol, isopropanol or the like or a mixture thereof.

The reaction temperature varies depending on the reaction conditions such as the type of base used, but it may generally be in the range of from $-78°$ C. to $100°$ C.

The reaction time may be set appropriately taking the reaction conditions into consideration.

In this instance, it is possible to produce an unsymmetric compound having different heterocyclic groups in the same manner as the procedure of the production process 1.

Production process 3

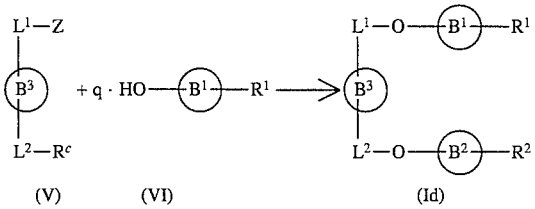

[In the above reaction formulae, each of $R^1$, $R^2$, $L^1$, $L^2$, $B^1$, $B^2$ and $B^3$ has the same meaning as described in the foregoing, Z represents a halogen atom, $R^c$ is a group represented by a formula

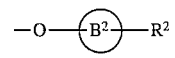

(where each of $B^2$ and $R^2$ has the same meaning as described in the foregoing) or a halogen atom and q is 2 when $R^c$ is a halogen atom or 1 in other cases.]

The compound of the present invention represented by the general formula (Id) is produced by allowing a mono- or bishalide represented by the general formula (V) to react with a phenol derivative represented by the formula (VI) in the presence of a base. This is a well known method for the synthesis of aromatic ether compounds.

The reaction conditions should be selected depending on the compound used, but it is preferable to use dimethylformamide as the solvent and potassium carbonate as the base. The reaction may be carried out with cooling depending on the base, but generally at room temperature or with heating.

In this instance, it is possible to produce an unsymmetric compound having different heterocyclic groups in the same manner as the procedure of the production process 1.

Production process 4

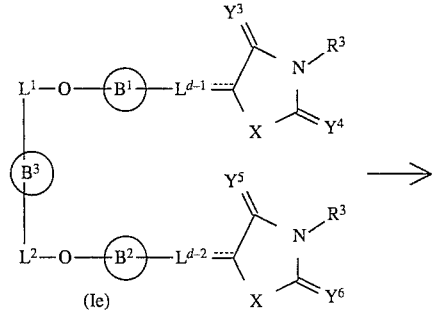

-continued
Production process 4

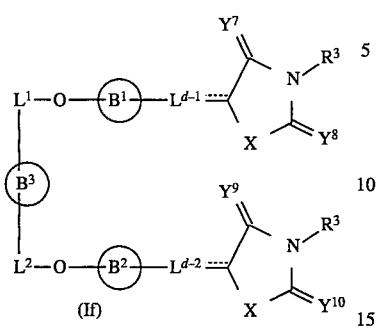
(If)

[In the above reaction formulae, each of $B^1$, $B^2$, $B^3$, $L^1$, $L^2$, X and $R^3$ has the same meaning as described in the foregoing, $L^{d-1}$ and $L^{d-2}$ may be the same or different from each other and each represents a methine group (—CH═) or a methylene group, at least one of $Y^3$, $Y^4$, $Y^5$ and $Y^6$ is sulfur atom and each of the rest is sulfur atom or oxygen atom, at least one of $Y^7$, $Y^8$, $Y^9$ and $Y^{10}$ is an oxygen atom and each of the rest is an oxygen atom or a sulfur atom and ▬ represents a single bond or a double bond.]

The carbonyl compound represented by the general formula (If) can be synthesized by an exchange reaction of thiocarbonyl for carbonyl in which the corresponding thiocarbonyl compound (Ie) is treated with an oxidizing agent.

The reaction can be effected in the absence of solvent, but preferably in an inert solvent including dimethylformamide, acetone, methylethylketone or an alcohol such as methanol, ethanol, isopropanol or the like. Preferred oxidizing agent may be selected from hydrogen peroxide and organic peroxides such as m-chloroperbenzoic acid, perbenzoic acid, monoperoxyphthalic acid, performic acid, peracetic acid, trifluoroperacetic acid and the like.

Though bases are not particularly required for the synthesis of the compound of this invention, it is possible to allow the compound (Ie) to undergo the reaction as an metal enolate of thiocarbonyl by adding a base such as sodium hydride.

The reaction can be fully effected at room temperature, or with cooling if necessary. The reaction time varies depending on the reaction conditions and therefore are set appropriately.

Production process 5

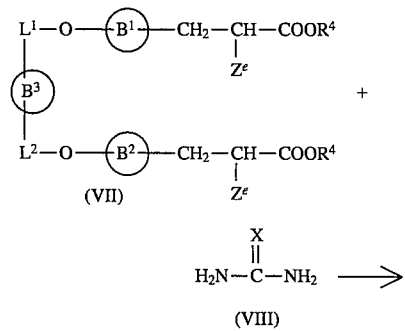
(VII)

$$\overset{X}{\underset{\|}{H_2N-C-NH_2}} \longrightarrow$$
(VIII)

-continued
Production process 5

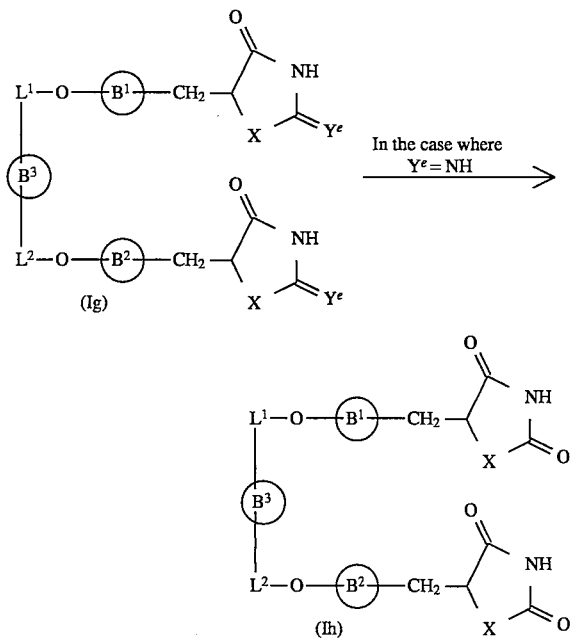

(In the above reaction formulae, each of $B^1$, $B^2$, $B^3$, $L^1$, $L^2$, X and $R^3$ has the same meaning as described in the foregoing, $R^4$ represents a hydrogen atom or an ester residue, $Z^e$ represents a halogen atom or hydroxyl group and $Y^e$ represents an imino group or an oxygen atom.)

The bis(oxazolidine or thiazolidine) derivative represented by the general formula (Ig) is produced by allowing a bis(halogenopropionic acid) derivative represented by the general formula (VII) to react with a thiourea or urea compound represented by the formula (VIII), and, when $Y^e$ of the compound (Ig) is an imino group, this is further hydrolyzed to produce the compound of the present invention bis(oxazolidine or thiazolidine) derivative represented by the general formula (Ih).

The ester residue represented by $R^4$ may be any group capable of forming an ester, which include lower alkyl groups such as methyl, ethyl, propyl, isopropyl, butyl, isobutyl, sec-butyl, tert-butyl, pentyl, isopentyl, neopentyl, sec-pentyl, tert-pentyl, hexyl, isohexyl and the like and aralkyl groups such as benzyl and the like.

This reaction is a heterocycle forming reaction and may be carried out in the absence or presence of an inert organic solvent which includes an alcohol such as methanol, ethanol, propanol, isopropanol, methoxyethanol, ethoxyethanol or the like, dimethylsulfoxide, dimethylformamide, N,N'-dimethylimidazolidinone or the like. Of these, alcohols are particularly preferable, when a case is taken into consideration in which the reaction solution is subjected directly to the subsequent acid hydrolysis step.

With regard to the amount of the starting compounds, the easily available compound (VIII) may be used in an excess amount.

The reaction may be carried out at a temperature of from 50° to 200° C., advantageously at the reflux temperature of the solvent used.

Though the reaction progresses sufficiently by heating only, it may be carried out generally in the presence of a catalyst such as sodium acetate or potassium acetate or sodium methoxide, potassium tert-butoxide or the like.

The reaction time may be set appropriately, taking the type of starting compounds, reaction conditions and the like into consideration.

In the case of the reaction when $Y^e$ in the formula (Ig) is an imino group, it is an exchange reaction of the imino group for carbonyl group, and the reaction is carried out in an inert solvent, particularly an alcohol, in the presence of excess amounts of water and an acid (e.g., strong acid such as hydrochloric acid, hydrobromic acid or the like) and generally with heating, preferably with reflux.

Production process 6

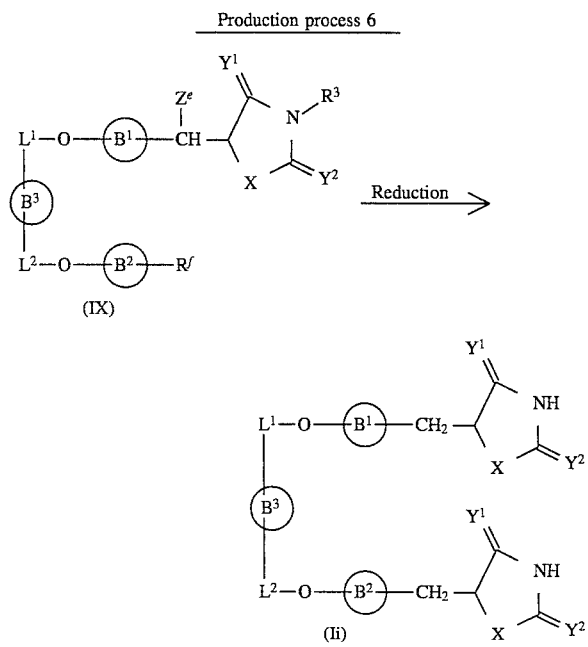

[In the above reaction formulae, each of $B^1$, $B^2$, $B^3$, $L^1$, $L^2$, $Z^e$, X, $Y^1$, $Y^2$ and $R^3$ has the same meaning as described in the foregoing and $R^f$ is a group represented by a formula:

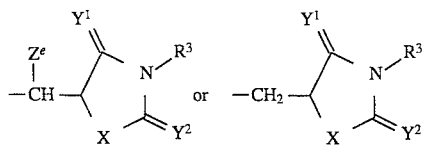

(where each of X, $Y^1$, $Y^2$, $R^3$, $Z^e$ and $R^2$ has the same meaning as described in the foregoing).]

Among the compounds of the present invention, the bisheterocyclic derivative represented by the general formula (Ii) is produced by carrying out reduction of a mono or bishalogeno- or hydroxy-bisheterocyclic derivative represented by the general formula (IX).

In this reaction, a halogenomethylene group or a hydroxymethylene group

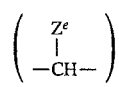

is converted into a methylene group and, when $R^3$ is a protective group, the protective group is simultaneously eliminated, advantageously by making use of a hydrogenation reaction with a catalyst such as palladium on carbon or the like in an organic solvent such as alcohol (e.g., methanol, ethanol or the like) generally at room temperature or with warming.

Production process 7

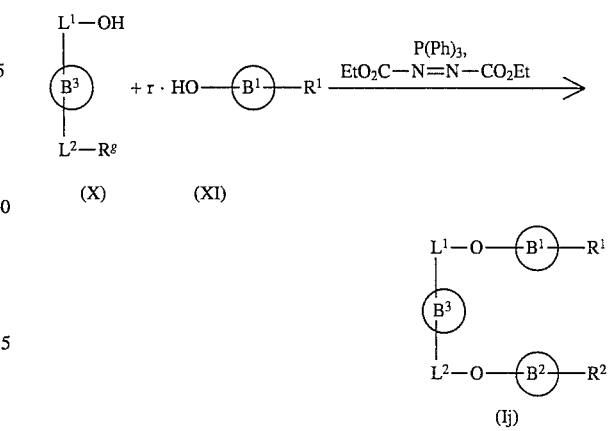

(In the above reaction formulae, each of $B^1$, $B^2$, $B^3$, $L^1$ and $L^2$ has the same meaning as described in the foregoing, $R^g$ is a hydroxyl group or a group represented by a formula $-O-B^2-R^2$ and r is 2 when $R^g$ is a hydroxyl group or 1 in other cases.)

The compound (Ij) of the present invention can be synthesized by the Mitsunobu reaction in which an ether compound is formed by allowing a mono- or bishydroxy compound represented by the general formula (X) to react with a phenol compound represented by the general formula (XI) in the presence of triphenylphosphine and diethyl azodicarboxylate.

It is desirable to carry out this reaction using one mol or two mols of the compound (XI) based on one mol of the compound (X), or either one in a slightly excess amount than its chemical equivalent, in an inert organic solvent such as ether, tetrahydrofuran, dioxane, benzene, toluene, xylene, dimethylformamide or the like, with cooling or at room temperature.

Production process 8

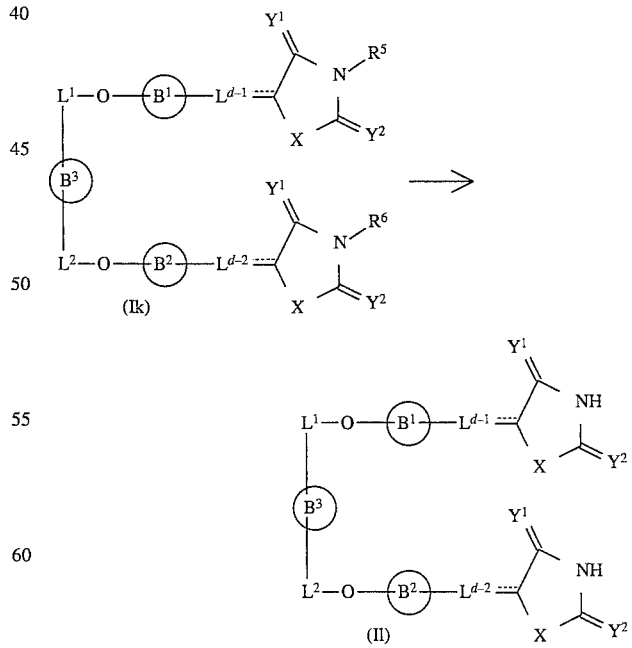

(In the above reaction formulae, each of $B^1$, $B^2$, $B^3$, $L^1$, $L^2$, $L^{d-1}$, $L^{d-2}$, X, $Y^1$, $Y^2$ and ___ has the same meaning as described in the foregoing and at least one of $R^5$ and $R^6$ is a protective group and the other is a hydrogen atom or a protective group.)

The compound of the present invention represented by the general formula (II) is produced by eliminating the protective group from a protective group-containing bisheterocyclic compound represented by the general formula (Ik).

Elimination of the protective group can be made easily by treating the compound with an acid, preferably with an organic peracid or mineral acid such as trifluoroperacid, hydrochloric acid or the like.

The thus produced compound (I) of the present invention is isolated and purified in its free form or as a salt.

Isolation and purification are carried out by making use of usual chemical procedures such as extraction, crystallization, recrystallization and various types of column chromatography, especially silica gel column chromatography.

INDUSTRIAL APPLICABILITY

Since the compound (I) according to the present invention and salts and the like thereof have excellent hypoglycemic effect based on their insulin sensitivity enhancing function and have low toxicity, they are useful as drugs for the prevention and treatment of diabetes, especially insulin-independent diabetes mellitus (type II), and various complications of diabetes and as concomitant drugs of insulin.

The hypoglycemic effect based on the insulin sensitivity enhancing function according to the present invention has been confirmed by the following test. Hypoglycemic activity Male kk mice of 4 to 5 weeks of age were purchased from Clea Japan Inc. The animals were individually reared with a high calorie food (CMF, Oriental Yeast Co., Ltd.) and used in the test when their body weights reached around 40 g.

The blood sugar level was determined by collecting 10 µl of a blood sample from the tail vein, removing protein from the sample with 100 µl of 0.33N perchloric acid, subjecting the thus treated sample to centrifugation and then measuring glucose content in the resulting supernatant fluid by the glucose oxidase method. Six animals with a blood sugar level of 200 mg/dl or more were used as a group for the test.

Each drug was suspended in 0.5% methyl cellulose solution, and its daily oral administration was carried out for 4 days. Blood samples were collected from the tail vein before and on the fifth day of the drug administration to measure their sugar levels in the same manner as described above.

The hypoglycemic activity was calculated as a decreasing ratio of the blood sugar level to the level before the drug administration and evaluated statistically setting the significant threshold value as $p=0.05$.

\*=$p<0.05$
\*\*=$p<0.01$
\*\*\*=$p<0.001$

Results of the test are shown in Table 1.

TABLE 1

| Example compound No. | Dose mg/day | Blood sugar decreasing ratio (%) |
|---|---|---|
| 1-b | 10 | 56 *** |
| 19-b | 30 | 32 * |
| 19-c | 10 | 51 ** |
| 20-c | 10 | 50 ** |
| 20-b | 30 | 32 ** |
| 22 | 30 | 57 *** |
| 9 | 10 | 53 *** |

A pharmaceutical preparation containing one or more of the compounds represented by the general formula (I) or the like as active ingredients may be prepared by making use of carriers, vehicles and other additives generally used in the drug making.

Solid or liquid nontoxic materials for pharmaceutical use may be used as carriers and vehicles in the pharmaceutical preparation. Their illustrative examples include lactose, magnesium stearate, starch, talc, gelatin, agar, pectin, gum arabic, olive oil, sesame oil, cacao butter, ethylene glycol and the like and other usually used materials.

In order to avoid troublesome handling such as insulin injection, similar to the case of the prior art synthetic hypoglycemic drugs such as sulfonylurea preparation and the like, the inventive pharmaceutical preparation may advantageously be made into oral dosage forms such as tablets, capsules, powders, fine subtilaes, granules, pills and the like, but it is also possible to make it into parenteral dosage forms such as injections, suppositories, plasters (including intraoral use), nasal forms and the like.

Clinical dose of the compound of the present invention is set optionally by taking into consideration symptoms, body weight, age, sex and the like of each patient to be treated, but it may generally be administered orally in a daily dose of from 10 to 2,000 mg per adult once a day or by dividing the daily dose into two or more portions.

BEST MODE FOR CARRYING OUT THE INVENTION

The following examples (chemical structures: Tables 1 to 7) are provided to further illustrate the present invention.

Example 1

In 100 ml of dimethylformamide were dissolved 21.02 g of trans 1,4-bis(4-formylphenoxy)methylcyclohexane, 14.04 g of 2,4-thiazolidinedione and 1.84 g of ammonium acetate, followed by 24 hours of reflux. Precipitated crystals were collected by filtration to obtain 20.14 g of trans 1,4-bis[[(4-[(2,4-dioxo-5-thiazolidinylidene)methyl]phenoxy]methyl]cyclohexane (1-a). This compound was suspended in 100 ml of dimethylimidazolidinone and 6.33 g of sodium borohydride was added to the suspension, subsequently stirring the mixture for 2 hours at 80° C. The resulting reaction solution was added to a mixture of 23 ml of concentrated hydrochloric acid with ice water and ethyl acetate to collect the organic layer. After washing with water, the organic layer was dried over magnesium sulfate and the solvent was distilled off. Thereafter, the resulting residue was purified by subjecting it to silica gel column chromatography (toluene:ethyl acetate (2:1)) to obtain 16.8 g of trans 1,4-bis[[(4-[(2,4-dioxo-5-thiazolidinyl)methyl]phenoxy]methyl]cyclohexane (1-b).

Physicochemical properties (1-a)

Melting point: >300° C. Mass spectrometry data (m/z): 550 (M-H)⁻ FAB (Neg.) Nuclear magnetic resonance spectrum (DMSO-$d_6$, TMS internal standard): δ: 1.00–1.20 (4H, m, cyclohexyl) 1.70–1.95 (6H, m, cyclohexyl) 3.89 (4H, d, O—$CH_2$) 7.09 (4H, d, phenyl) 7.54 (4H, d, phenyl)

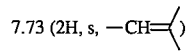

12.45 (2H, bs, NH)
Physicochemical properties (1-b)

Melting point: 247°–8° C.

| Elemental analysis data (for $C_{28}H_{30}N_2O_6S_2$): | | | | |
|---|---|---|---|---|
| | C (%) | H(%) | N(%) | S(%) |
| calculated | 60.63 | 5.45 | 5.05 | 11.56 |
| found | 61.08 | 5.48 | 4.84 | 11.73 |

Mass spectrometry data (m/z): 553 (M-1)$^+$ FAB (Neg.)
Nuclear magnetic resonance spectrum (DMSO-$d_6$, TMS internal standard): δ: 1.00–1.15 (4H, m, cyclohexyl)

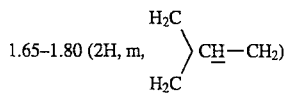

1.65–1.80 (2H, m, 1.80–1.95 (4H, m, cyclohexyl)

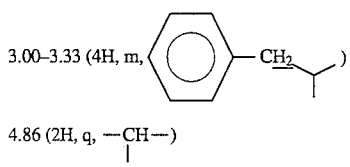

3.00–3.33 (4H, m, 4.86 (2H, q, —CH—)

6.86 (4H, d, phenyl) 7.13 (4H, d, phenyl) 12.00 (2H, bs, NH)

The following compounds of Examples 2 to 7 were obtained in the same manner.

Example 2

1,4-Bis[5-[4-[(2,4-dioxo-5-thiazolidinyl)methyl]phenoxy]-pentoxy]benzene
Starting compound: 1,4-bis[5-(4-formylphenoxy)pentoxy]benzene
Physicochemical properties
Melting point: 104°–5° C. methanol

| Elemental analysis data (for $C_{36}H_{40}N_2O_8S_2$): | | | | |
|---|---|---|---|---|
| | C (%) | H(%) | N(%) | S(%) |
| calculated | 62.41 | 5.82 | 4.04 | 9.26 |
| found | 62.36 | 5.83 | 3.85 | 9.38 |

Mass spectrometry data (m/z): 691 (M-H)$^-$ FAB (Neg.)
Nuclear magnetic resonance spectrum (DMSO-$d_6$, TMS internal standard): δ: 1.44–1.80 (12H, m, OCH$_2$C$\underline{H}_2$C$\underline{H}_2$CH$_2$CH$_2$O)

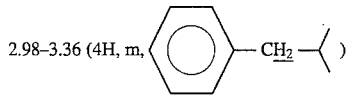

2.98–3.36 (4H, m, 3.84–4.00 (8H, m, O—CH$_2$—)

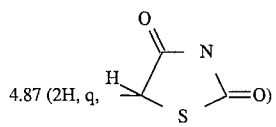

4.87 (2H, q, 6.80–7.20 (12H, m, phenyl) 12.00–(2H, bs, NH)

Example 3

1,3-Bis[5-[4-[(2,4-dioxo-5-thiazolidinyl)methyl]phenoxy]pentoxy]benzene

Starting compound: 1,3-bis[5-(4-formylphenoxy)pentoxy]benzene
Physicochemical properties
Melting point: 79°–80° C. (methanol)

| Elemental analysis data (for $C_{36}H_{40}N_2O_8S_2$): | | | | |
|---|---|---|---|---|
| | C (%) | H(%) | N(%) | S(%) |
| calculated | 62.41 | 5.82 | 4.04 | 9.26 |
| found | 62.15 | 5.82 | 3.86 | 9.40 |

Mass spectrometry data (m/z): 691. (M-H)$^-$ FAB (Neg.)
Nuclear magnetic resonance spectrum (DMSO-$d_6$, TMS internal standard): δ: 1.44–1.84 (12H, m, OCH$_2$C$\underline{H}_2$C$\underline{H}_2$CH$_2$CH$_2$O)

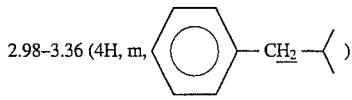

2.98–3.36 (4H, m, 3.96 (8H, t, O—CH$_2$—)

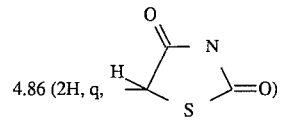

4.86 (2H, q, 6.46–7.24 (12H, m, phenyl) 12.00–(2H, bs, NH)

Example 4

1,2-Bis[5-[4-[(2,4-dioxo-5-thiazolidinyl)methyl]phenoxy]pentoxy]benzene
Starting compound: 1,2-bis[5-(4-formylphenoxy)pentoxy]benzene
Physicochemical properties
Melting point: resinous
Mass spectrometry data (m/z): 691 (M-H)$^-$ FAB (Neg.)
Nuclear magnetic resonance spectrum (DMSO-$d_6$, TMS internal standard): δ: 1.44–1.80 (12H, m, OCH$_2$C$\underline{H}_2$C$\underline{H}_2$CH$_2$CH$_2$O)

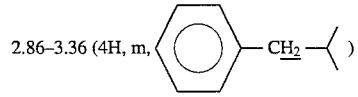

2.86–3.36 (4H, m, 3.84–4.00 (8H, m, O—CH$_2$—)

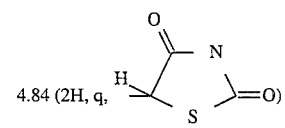

4.84 (2H, q, 6.76–7.12 (12H, m, phenyl) 11.99 (2H, bs, NH)

Example 5

1,2-Bis[4-[(2,4-dioxo-5-thiazolidinyl)methyl]phenoxy]benzene
Starting compound: 1,2-bis(4-formylphenoxy)benzene
Physicochemical properties Melting point: resinous Elemental analysis data (for $C_{26}H_{20}N_2O_6S_2 \cdot 0.7H_2O$):

|  | C (%) | H(%) | N(%) | S(%) |
|---|---|---|---|---|
| calculated | 58.57 | 4.05 | 5.25 | 12.03 |
| found | 58.31 | 3.78 | 5.15 | 12.14 |

Mass spectrometry data (m/z): 519 (M-H)⁻ FAB (Neg.)
Nuclear magnetic resonance spectrum (DMSO-$d_6$, TMS internal standard):

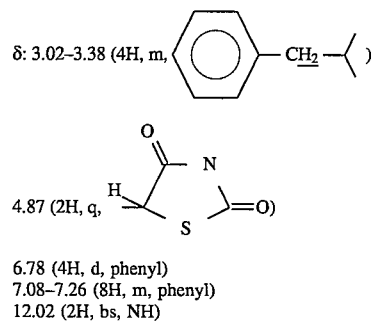

6.78 (4H, d, phenyl)
7.08–7.26 (8H, m, phenyl)
12.02 (2H, bs, NH)

Example 6

1,4-Bis[4-[(2,4-dioxo-5-thiazolidinyl)methyl]phenoxy]benzene
Starting compound: 1,4-bis(4-formylphenoxy)benzene
Physicochemical properties
  Melting point: 203°–4° C.

Elemental analysis data (for $C_{26}H_{20}N_2O_6S_2$):

|  | C (%) | H(%) | N(%) | S(%) |
|---|---|---|---|---|
| calculated | 59.99 | 3.87 | 5.38 | 12.32 |
| found | 59.83 | 4.03 | 5.21 | 12.24 |

Mass spectrometry data (m/z): 521 (MH⁺) FAB (Pos.)
Nuclear magnetic resonance spectrum (DMSO-$d_6$, TMS internal standard):

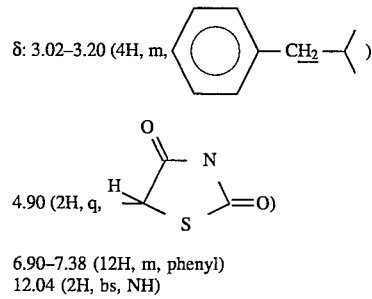

6.90–7.38 (12H, m, phenyl)
12.04 (2H, bs, NH)

Example 7

Cis 1,4-bis[[4-[(2,4-dioxo-5-thiazolidinyl)methyl]phenoxy]methyl]cyclohexane
Starting compound: cis 1,4-bis[(4-formylphenoxy)methyl]cyclohexane
Physicochemical properties Melting point: 186°–7° C. (methanol)

Elemental analysis data (for $C_{28}H_{30}N_2O_6S_2$):

|  | C (%) | H(%) | N(%) | S(%) |
|---|---|---|---|---|
| calculated | 60.63 | 5.45 | 5.05 | 11.56 |
| found | 60.53 | 5.50 | 4.96 | 11.43 |

Mass spectrometry data (m/z): 553 (M-H)⁻ FAB (Neg.)
Nuclear magnetic resonance spectrum (DMSO-$d_6$, TMS internal standard):

δ: 1.40–1.60 (8H, m, cyclohexyl)

1.85–2.00 (2H, m, ...)

3.00–3.35 (4H, m, ...)

3.87 (4H, d, O—CH₂—...)

4.86 (2H, q, ...)

6.87 (4H, d, phenyl)

7.14 (4H, d, phenyl)

12.00 (2H, bs, NH)

Example 8

A 5.6 g portion of 1,3-bis(4-aminophenoxy)benzene was dissolved in 100 ml of acetone and 15 ml of water, and 11.2 ml of concentrated hydrochloric acid was added to the resulting solution. With cooling on an ice bath and with stirring, to this was added dropwise 3.04 g of sodium nitrite dissolved in 10 ml of water. To this were added 24 ml of methyl acrylate and, after heating to 40° C., 0.55 g of cuprous oxide, followed by 15 minutes of stirring at the same temperature. After spontaneous cooling, ethyl acetate was added to the reaction mixture to separate and collect the organic layer which was subsequently washed with 1N hydrochloric acid, water and saturated sodium chloride solution in that order, dried over magnesium sulfate and then subjected to distillation to remove the solvent. The resulting residue was dissolved in 100 ml of ethanol, followed by the addition of 3.06 g of thiourea and 3.30 g of sodium acetate and subsequent overnight reflux. After adding 120 ml of 4N hydrochloric acid, the mixture was subjected to overnight reflux and then the solvent was removed by distillation. Water and ethyl acetate were added to the resulting residue to separate and collect the organic layer which was subsequently washed with saturated sodium chloride solution, dried over magnesium sulfate and then subjected to distillation to remove the solvent. The resulting residue was subjected to silica gel column chromatography (benzene-:ethyl acetate (3:1)) to obtain 2.10 g of 1,3-bis[4-[(2,4-dioxo-5-thiazolidinyl)methyl]phenoxy]benzene.
Physicochemical properties Melting point: resinous Mass spectrometry data (m/z): 519 (M-H)⁺ FAB (Neg.) Nuclear magnetic resonance spectrum (DMSO-$d_6$, TMS internal standard):

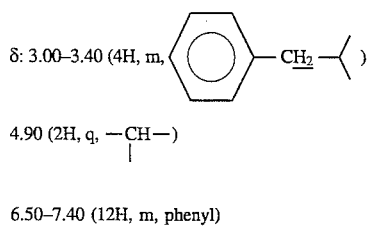

The following compounds of Examples 9 to 11 were obtained in the same manner.

Example 9

1,3-Bis[4-[(2,4-dioxo-5-thiazolidinyl)methyl]phenoxy]-cyclohexane
Starting compound: 1,3-bis(4-aminophenoxy)cyclohexane
Physicochemical properties
Melting point: resinous Mass spectrometry data (m/z): 525 (M-H)⁻ FAB (Neg.) Nuclear magnetic resonance spectrum (DMSO-$d_6$, TMS internal standard):

δ: 1.20–2.50 (8H, m, cyclohexyl)

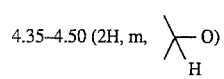

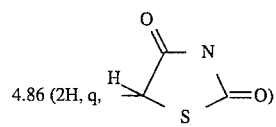

6.90 (4H, d, phenyl)
7.13 (4H, d, phenyl)
12.00 (2H, bs, NH)

Example 10

Cis 1,4-bis[4-[(2,4-dioxo-5-thiazolidinyl)methyl]phenoxy] cyclohexane
Starting compound: 1,4-bis(4-aminophenoxy)cyclohexane
Physicochemical properties
Melting point: 241°–2° C. Mass spectrometry data (m/z): 515 (M-H)⁻ FAB (Neg.) Nuclear magnetic resonance spectrum (DMSO-$d_6$, TMS internal standard):

δ: 1.60–2.00 (8H, m, cyclohexyl)

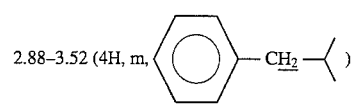

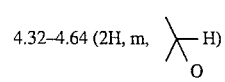

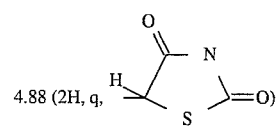

6.92 (4H, d, phenyl)
7.16 (4H, d, phenyl)
12.02 (2H, bs, NH)

Example 11

Trans 1,4-bis[4-[(2,4-dioxo-5-thiazolidinyl)methyl]phenoxy]cyclohexane
Starting compound: 1,4-bis(4-aminophenoxy)cyclohexane
Physicochemical properties
Melting point: 259°–260° C. Mass spectrometry data (m/z): 553 (M-H)⁻ FAB (Neg.) Nuclear magnetic resonance spectrum (DMSO-$d_6$, TMS internal standard):

δ: 1.44–1.90 (8H, m, cyclohexyl)

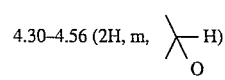

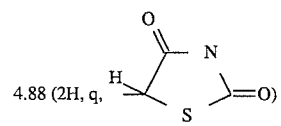

6.90 (4H, d, phenyl)
7.16 (4H, d, phenyl)
12.01 (2H, bs, NH)

Example 12

A 2.23 g portion of 2,4-dioxo-5-[(p-hydroxyphenyl)-methyl]thiazolidine was dissolved in 25 ml of dimethylformamide, and the solution was mixed with 0.8 g of sodium hydride and maintained at 60° C. for 3 hours. Under cooling with ice water, 1.32 g of p-xylylene dibromide was added to the solution, and the mixture was incubated at room temperature for 3 hours and then at 80° C. for 3 hours. A 100 ml portion of water and 100 ml of ethyl acetate were added to the reaction mixture to dissolve insoluble contents, and the resulting organic layer was collected and washed with water, followed by distillation to remove ethyl acetate. Thereafter, the resulting residue was subjected to silica gel column chromatography (eluent: chloroform) to obtain 1,4-bis[[4-[(2,4-dioxo-5-thiazolidinyl)methyl]phenoxy]methyl]benzene.
Physicochemical properties
Melting point: 221°–224° C. (methanol)

| | Elemental analysis data (for $C_{28}H_{24}N_2O_6S_2$): | | | |
|---|---|---|---|---|
| | C (%) | H(%) | N(%) | S(%) |
| calculated | 61.30 | 4.41 | 5.11 | 11.69 |
| found | 61.19 | 4.46 | 4.99 | 11.67 |

Mass spectrometry data (m/z): 547 (M-H)⁻ FAB (Neg.) Nuclear magnetic resonance spectrum (DMSO-$d_6$, TMS internal standard): δ: 3.05 (2H, dd, —CHH—) 3.30 (2H, dd, —CHH—)

4.88 (2H, dd, —CH—)

5.1 (4H, s, —O—CH$_2$—) 6.97 (4H, d, phenyl) 7.18 (4H, d, phenyl) 7.48 (4H, s, phenyl) 12.01 (2H, brs, NH)

The following compounds of Examples 13 and 14 were obtained in the same manner.

Example 13

1,3-Bis[[4-[(2,4-dioxo-5-thiazolidinyl)methyl]phenoxy]methyl]benzene
Starting compound: m-xylene dibromide
Physicochemical properties
Melting point: 159°–164° C. (methanol)

| Elemental analysis data (for C$_{28}$H$_{24}$N$_2$O$_6$S$_2$): | | | | |
|---|---|---|---|---|
| | C (%) | H(%) | N(%) | S(%) |
| calculated | 61.30 | 4.41 | 5.11 | 11.69 |
| found | 61.29 | 4.49 | 4.91 | 11.63 |

Nuclear magnetic resonance spectrum (DMSO-d$_6$, TMS internal standard): δ: 3.05 (2H, dd, —C<u>H</u>H—)

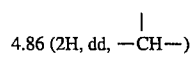

4.86 (2H, dd, —CH—)

5.08 (4H, s, —O—CH$_2$—) 6.95 (4H, d, phenyl) 7.16 (4H, d, phenyl) 7.40 (3H, s, phenyl) 7.52 (1H, s, phenyl) 12.01 (2H, s, NH)

Example 14

1,2-Bis[[4-[(2,4-dioxo-5-thiazolidinyl)methyl]phenoxy]methyl]benzene
Starting compound: o-xylene dibromide
Physicochemical properties
Melting point: resinous

| Elemental analysis data (for C$_{28}$H$_{24}$N$_2$O$_6$S$_2$): | | | | |
|---|---|---|---|---|
| | C (%) | H(%) | N(%) | S(%) |
| calculated | 61.30 | 4.41 | 5.11 | 11.69 |
| found | 61.09 | 4.50 | 4.88 | 11.57 |

Mass spectrometry data (m/z): 547 (M-H)$^-$ FAB (Neg.) Nuclear magnetic resonance spectrum (DMSO-d$_6$, TMS internal standard): δ: 3.05 (2H, dd, —C<u>H</u>H—)

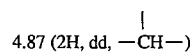

4.87 (2H, dd, —CH—)

5.20 (4H, s, —O—CH$_2$—) 6.97 (4H, d, phenyl) 7.16 (4H, d, phenyl) 7.36 (2H, m, phenyl) 7.52 (2H, m, phenyl) 12.01 (2H, brs, NH)

Example 15

A 14.6 g portion of isosorbide, 35 g of p-fluorobenzaldehyde and 34 g of anhydrous potassium carbonate were added to 100 ml of dimethylsulfoxide and heated at 160° C. for 24 hours with stirring. After completion of the reaction, 200 ml of water and 300 ml of ethyl acetate were added to the reaction solution to separate liquid phases, the resulting organic layer was washed with water and subjected to distillation to remove ethyl acetate and then the resulting oily material was subjected to silica gel column chromatography (eluent: chloroform) to collect eluates after elution of excess p-fluorobenzaldehyde, thereby obtaining 4.5 g of O,O'-bis(p-formylphenyl)isosorbide.

A 4.5 g portion of the thus obtained formylphenyl derivative was subjected to 72 hours of reflux with stirring together with 3.5 g of 2,4-dioxothiazolidine, 0.7 g of ammonium acetate and 50 ml of acetic acid, and crystals thus formed were collected by filtration while hot and washed with acetic acid to obtain crude O,O'-bis[4-[(2,4-dioxo-5-thiazolidinylidene)methyl]phenyl]isosorbide (15-a).

A 5.5 g portion of the thus obtained thiazolidinylidene derivative and 5.5 g of sodium borohydride were dissolved in 50 ml of dimethylimidazolidinone and heated at 70° C. for 12 hours. After completion of the reaction, the reaction solution was dispersed in a mixed solvent consisting of 100 ml of ice water, 200 ml of ethyl acetate and 20 ml of hydrochloric acid, and the thus formed organic layer was collected, washed with water and then subjected to distillation to remove ethyl acetate. The resulting residue was subjected to silica gel column chromatography (eluent: chloroform) to collect eluates of Rf=0.1, thereby obtaining O,O'-bis[4-[(2,4-dioxo-5-thiazolidinyl)methyl]phenyl]isosorbide (15-b).

Physicochemical properties (15-a) Mass spectrometry data (m/z): 551 (M-H)$^-$ FAB (Neg.) Nuclear magnetic resonance spectrum (DMSO-d$_6$, TMS internal standard): δ: 3.92 (2H, m) 4.03 (2H, m) 4.59 (1H, d) 5.06 (3H, m) 7.1–7.2 (4H, dd, phenyl) 7.5–7.6 (4H, m, phenyl)

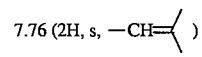

12.53 (2H, brs, NH)
Physicochemical properties (15-b)
Melting point: resinous

| Elemental analysis data (for C$_{26}$H$_{24}$N$_2$O$_8$S$_2$): | | | | |
|---|---|---|---|---|
| | C (%) | H(%) | N(%) | S(%) |
| calculated | 56.10 | 4.35 | 5.03 | 11.52 |
| found | 55.63 | 4.63 | 5.85 | 11.19 |

Mass spectrometry data (m/z): 555 (M-H)$^-$ FAB (Neg.) Nuclear magnetic resonance spectrum (DMSO-d$_6$, TMS internal standard): δ: 3.03–3.1 (2H, m, —C<u>H</u>H—) 3.7–4.0 (2H, m) 4.0–4.1 (2H, m) 4.5 (1H, m) 4.8–4.9 (5H, m) 6.94 (4H, m, phenyl) 7.17 (4H, m, phenyl) 12.01 (2H, brs, NH)

The following compounds of Examples 16 to 18 were obtained in the same manner.

Example 16

O,O'-Bis[4-[(2,4-dioxo-5-thiazolidinyl)methyl]phenyl]isomannide
Physicochemical properties
Melting point: 269°–70° C. (methanol)

| Elemental analysis data (for C$_{26}$H$_{24}$N$_2$O$_8$S$_2$): | | | | |
|---|---|---|---|---|
| | C (%) | H(%) | N(%) | S(%) |
| calculated | 56.10 | 4.35 | 5.03 | 11.52 |
| found | 56.03 | 4.35 | 5.03 | 11.73 |

Mass spectrometry data (m/z): (M-H)$^-$ FAB (Neg.) Nuclear magnetic resonance spectrum (DMSO-d$_6$, TMS internal standard): δ: 3.06 (2H, dd, —C<u>H</u>H—) 3.31 (2H, dd, —CH<u>H</u>—) 3.74 (2H, t-like) 4.02 (2H, t-like) 4.8–4.9 (6H, m) 6.97 (4H, m, phenyl) 7.15 (4H, m, phenyl) 12.02 (2H, brs, NH)

Example 17

2,7-Bis[4-[(2,4-dioxo-5-thiazolidinyl)methyl]phenoxy]naphthalene
Starting compound: 2,7-dihydroxynaphthalene
Physicochemical properties
  Melting point: resinous Elemental analysis data (for $C_{30}H_{22}N_2O_6S_2$):

|  | C (%) | H(%) | N(%) | S(%) |
|---|---|---|---|---|
| calculated | 63.14 | 3.89 | 4.91 | 11.24 |
| found | 63.20 | 4.00 | 4.91 | 11.34 |

Mass spectrometry data (m/z): 569 (M-H)⁻ FAB (Neg.)
Nuclear magnetic resonance spectrum (DMSO-$d_6$, TMS internal standard): δ: 3.13 (2H, dd, —C$\underline{H}$H—) 3.38 (2H, dd, —CH$\underline{H}$—)

4.91 (2H, dd, —CH—)

6.9–7.4 (12H, m, phenyl) 7.95 (2H, d, phenyl) 12.04 (2H, brs, NH)

Example 18 (18-a)

2,6-Bis[4-[(2,4-dioxo-5-thiazolidinylidene)methyl]phenoxy]naphthalene
Starting compound: 2,6-dihydroxynaphthalene
Physicochemical properties
  Mass spectrometry data (m/z): 565 (M-H)⁻ FAB (Neg.)
Nuclear magnetic resonance spectrum (DMSO-$d_6$, TMS internal standard): δ: 7.1–7.3 (4H, m, phenyl) 7.35–7.4 (2H, m, phenyl) 7.6–7.67 (6H, d-like, phenyl) 7.9–8.02 (2H, m, phenyl)

7.8 (2H, s, —CH=⟨ )

12.57 (2H, brs, NH)
(18-b)
2,6-Bis[4-[(2,4-dioxo-5-thiazolidinyl)methyl]phenoxy]naphthalene
Starting compound: 2,6-dihydroxynaphthalene
Physicochemical properties
  Melting point: 212°–6° C. (methanol)

Elemental analysis data (for $C_{30}H_{22}N_2O_6S_2$):

|  | C (%) | H(%) | N(%) | S(%) |
|---|---|---|---|---|
| calculated | 63.14 | 3.89 | 4.91 | 11.24 |
| found | 62.94 | 3.99 | 4.63 | 11.54 |

Mass spectrometry data (m/z): 596 (M-H)⁻ FAB (Neg.)
Nuclear magnetic resonance spectrum (DMSO-$d_6$, TMS internal standard): δ: 3.14 (2H, dd, —C$\underline{H}$H—)

4.92 (2H, dd, —CH—)

6.9–7.9 (14H, m, phenyl) 12.05 (2H, brs, NH)

Example 19

(1) A mixture consisting of 3.52 g of trans-1,4-bis[[4-formylphenoxy)methyl]cyclohexane, 2.34 g of 4-oxo-2-thioxooxazolidine, 0.31 g of sodium acetate and 50 ml of acetic acid was subjected to overnight reflux. After spontaneous cooling, crystals thus formed were collected by filtration and recrystallized from dimethylformamide to obtain 3.75 g of trans-1,4-bis[[4-[(4-oxo-2-thioxo-5-oxazolidinylidene)methyl]phenoxy]methyl]cyclohexane (19-a).

(2) A 4.85 g portion of the compound obtained in the above step (1) was dissolved in 150 ml of dimethylformamide, and 7.60 g of methachloroperbenzoic acid was added to the solution and stirred for 2 hours at room temperature. After adding water to the reaction solution, the resulting precipitate was collected by filtration and recrystallized from dimethylformamide to obtain 3.23 g of trans-1,4-bis[[4-[(2,4-dioxo-5-oxazolidinylidene)methyl]phenoxy]methyl]cyclohexane (19-b).

(3) A 3.2 g portion of the compound obtained in the above step (2) and 3.5 g of 10% palladium on carbon were added to 100 ml of dimethylformamide and stirred for 3 hours in an atmosphere of hydrogen. After passing the reaction mixture through Celite to remove the catalyst, the filtrate was concentrated and the resulting residue was subjected to silica gel column chromatography (hexane-tetrahydrofuran (1:1)) to obtain 460 mg of trans-1,4-bis[[4-[(2,4-dioxo-5-oxazolidinyl)methyl]phenoxy]methyl]cyclohexane (19-c).

Physicochemical properties (19-a)
Nuclear magnetic resonance spectrum (DMSO-$d_6$, TMS internal standard):

δ:0.95–1.30 (4H, m, cyclohexyl),
1.60–2.05 (6H, m, cyclohexyl), 3.80 (4H, m, ⟩—CH₂O— x 2), 6.76 (2H, s, ...) N x 2), 7.10 (4H, d, phenyl), 7.80 (4H, d, phenyl)

Physicochemical properties (19-b)
Melting point: >300° C. Mass spectrometry data (m/z): 517 (FAB (Neg.))

δ:1.00–1.20 (4H, m, cyclohexyl),
1.70–1.95 (6H, m, cyclohexyl), 3.86 (4H, d, ⟩—CH₂O— x 2), 6.55 (2H, s, ...) N x 2), 7.03 (4H, d, phenyl), 7.70 (4H, d, phenyl)

Physicochemical properties (19-c)

Melting point: 218°–9° C.

| Elemental analysis data (for $C_{28}H_{30}N_2O_8$): | | | |
|---|---|---|---|
| | C (%) | H(%) | N(%) |
| calculated | 64.36 | 5.79 | 5.36 |
| found | 64.28 | 5.99 | 5.12 |

Mass spectrometry data (m/z): 521 (FAB (Neg.)) Nuclear magnetic resonance spectrum (DMSO-$d_6$, TMS internal standard):

δ:1.05–1.11 (4H, m, cyclohexyl),
1.65–1.90 (6H, m, cyclohexyl),

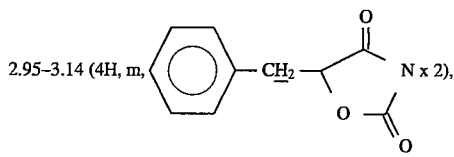

2.95–3.14 (4H, m, ... N x 2),

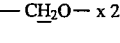

3.76 (4H, d, ...—CH₂O— x 2),

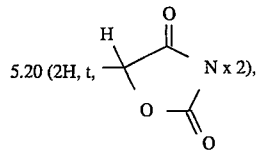

5.20 (2H, t, ... N x 2), 6.85 (4H, d, phenyl), 7.10 (4H, d, phenyl)

The following compounds of Example 20 were obtained in the same manner.

Example 20

20-a:
1,3-Bis[4-[(2-thioxo-4-oxo-5-oxazolidinylidene)methyl]phenoxy]benzene
Physicochemical properties
Nuclear magnetic resonance spectrum (DMSO-$d_6$): δ: 6.75–7.00 (3H, m, phenyl),

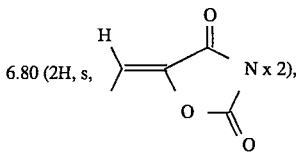

6.80 (2H, s, ... N x 2), 7.19 (4H, d, phenyl), 7.39–7.60 (1H, m, phenyl), 7.89 (4H, d, phenyl)

20-b:
1,3-Bis[4-[(2,4-dioxo-5-oxazolidinylidene)methyl]phenoxy]benzene
Physicochemical properties
Melting point: 273°–4° C. Nuclear magnetic resonance spectrum (DMSO-$d_6$, TMS internal standard): δ: 6.70–7.00 (3H, m, phenyl),

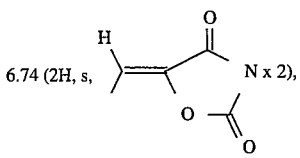

6.74 (2H, s, ... N x 2), 7.15 (4H, d, phenyl x 2), 7.35–7.60 (1H, m, phenyl), 7.81 (4H, d, phenyl)

20-c:
1,3-Bis[4-[(2,4-dioxo-5-oxazolidinyl)methyl]phenoxy]benzene
Physicochemical properties
Melting point: 183°–4° C.

| Elemental analysis data (for $C_{26}H_{20}N_2O_8$): | | | |
|---|---|---|---|
| | C (%) | H(%) | N(%) |
| calculated | 63.93 | 4.13 | 5.74 |
| found | 63.97 | 4.30 | 5.59 |

Mass spectrometry data (m/z): 487 (FAB (Neg.)) Nuclear magnetic resonance spectrum (DMSO-$d_6$, TMS internal standard):

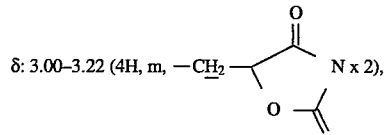

δ: 3.00–3.22 (4H, m, —CH₂— ... N x 2),

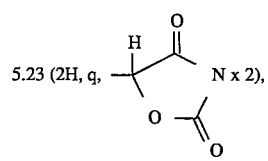

5.23 (2H, q, ... N x 2), 6.58–6.71 (3H, m, phenyl), 7.01 (4H, d, phenyl), 7.25 (4H, d, phenyl), 7.32–7.38 (1H, m, phenyl)

Example 21

(1) To a mixed solution consisting of 0.83 ml of n-butyllithium (1.6 mol hexane solution), 0.25 ml of diisopropylamine and 2 ml of tetrahydrofuran, cooled at −78° C., was added 0.31 g of 2,4-dioxo-3-trityloxazolidine which has been dissolved in 4 ml of tetrahydrofuran, followed by 30 minutes of stirring at the same temperature. A 0.14 g portion of 1,4-bis(4-formylphenoxy)benzene dissolved in 4 ml of tetrahydrofuran was added to the reaction solution and stirred for 30 minutes at the same temperature. After completion of the reaction, the reaction mixture was dispersed in 10 ml of saturated ammonium chloride aqueous solution and 20 ml of ethyl acetate to separate and collect the resulting organic layer. After washing the organic layer and distilling off the solvent, the resulting residue was mixed with 5 ml of acetonitrile and 0.087 ml of thionyl chloride and stirred for 1 hour at room temperature. By distilling off the solvent, 1,4-bis[4-[(2,4-dioxo-3-trityl-5-oxazolidinylchloromethyl)]phenoxy]benzene was obtained in an oily form. This compound was subjected to the subsequent step without purification.

(2) The compound obtained in the above step (1) and 0.2 g of 10% palladium on carbon were added to 3 ml of acetic acid and stirred for 12 hours in an atmosphere of hydrogen. After passing the reaction mixture through Celite to remove the catalyst, the filtrate was concentrated and the resulting residue was subjected to silica gel column chromatography (hexane-tetrahydrofuran (1:1)) to obtain 50 mg of 1,4-bis[4-[(2,4-dioxo-5-oxazolidinyl)methyl]phenoxy]benzene.
Physicochemical properties Melting point: 93°–96° C. Mass spectrometry data (m/z): 487 (M-H)⁻ (FAB (Neg.)) Nuclear magnetic resonance spectrum (TMS internal standard):

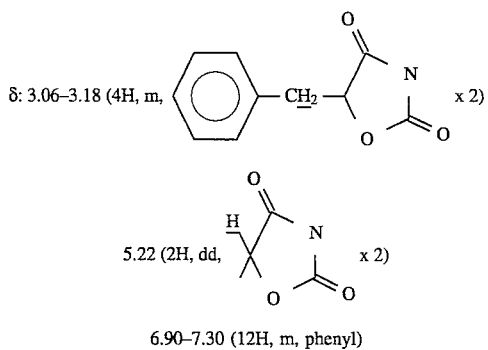

6.90–7.30 (12H, m, phenyl)

Example 22

A mixture consisting of 2.50 g of 1,3-bis[4-[(2-ethoxycarbonyl-2-hydroxy)ethyl]phenoxy]cyclohexane, 0.66 g of urea, 2.1 ml of sodium methylate (28% methanol solution) and 30 ml of ethanol was stirred at room temperature for 1 hour and then subjected to 3 hours of reflux. After spontaneous cooling and subsequent removal of the solvent by distillation, the resulting residue was mixed with water and ethyl acetate and neutralized with 4N hydrochloric acid to collect the separated organic layer. The organic layer was washed with saturated sodium chloride aqueous solution and dried over magnesium sulfate, followed by distillation removal of the solvent. The resulting residue was subjected to silica gel column chromatography (hexane-tetrahydrofuran (1:1)) to obtain 0.84 g of 1,3-bis[4-[(2,4-dioxo-5-oxazolidinyl)methyl]phenoxy]cyclohexane.

Physicochemical properties

Melting point: amorphous

| Elemental analysis data (for $C_{26}H_{26}N_2O_8$): | | | |
|---|---|---|---|
| | C (%) | H (%) | N (%) |
| calculated | 63.15 | 5.30 | 5.67 |
| found | 63.17 | 5.48 | 5.45 |

Mass spectrometry data (m/z): 493 (M-H)⁻ (FAB (Neg.)) Nuclear magnetic resonance spectrum (DMSO-$d_6$, TMS internal standard):

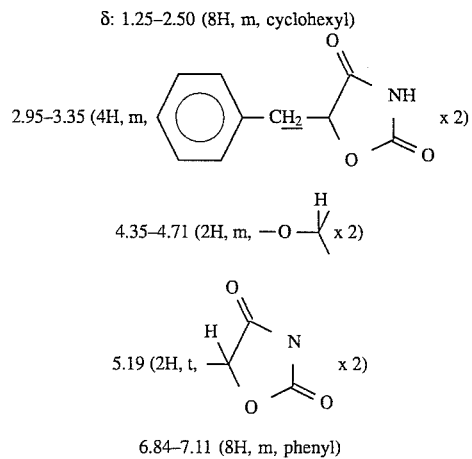

6.84–7.11 (8H, m, phenyl)

Example 23

A 2.52 g portion of 4-[(2,4-dioxo-3-trityl-5-oxazolidinyl)methyl]phenol, 329 mg of p-xylene glycol and triphenylphosphine were mixed with 50 ml of dry tetrahydrofuran in an atmosphere of argon. To the thus obtained homogeneous solution was added 977 mg of diethyl azodicarboxylate in a dropwise manner at 0° C. After 3 days of stirring at room temperature, the solvent was removed from the reaction mixture and the resulting residue was purified by silica gel column chromatography (chloroform) to obtain 1,4-bis[[4-[(2,4-dioxo-3-trityl-5-oxazolidinyl)methyl]phenoxy]methyl]benzene.

Physicochemical properties

Mass spectrometry data (m/z): 999 (M-H)⁻ (FAB (Neg.)) Nuclear magnetic resonance spectrum (CDCl₃, TMS internal standard):

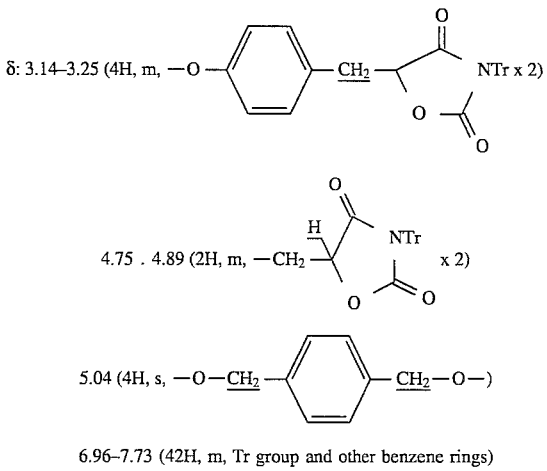

6.96–7.73 (42H, m, Tr group and other benzene rings)

Example 24

A 10 ml portion of trifluoroacetic acid was added to 220 mg of the product of Example 23, and the mixture was stirred for 4 hours at room temperature. The reaction mixture was diluted with ethyl acetate (100 ml), washed with water, saturated sodium bicarbonate aqueous solution, water and saturated sodium chloride aqueous solution in that order and then dried over anhydrous sodium sulfate. After distilling off the solvent, the resulting residue was purified by subjecting it to silica gel column chromatography (toluene-ethyl acetate, 1:1) to obtain 1,4-bis[[4-[(2,4-dioxo-5-oxazolidinyl)methyl]phenoxy]methyl]benzene.

Physicochemical properties

Mass spectrometry data (m/z): 515 (M⁺-H) (FAB (Neg.)) Nuclear magnetic resonance spectrum (DMSO-$d_6$, TMS internal standard):

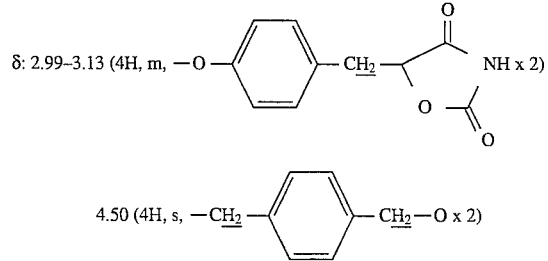

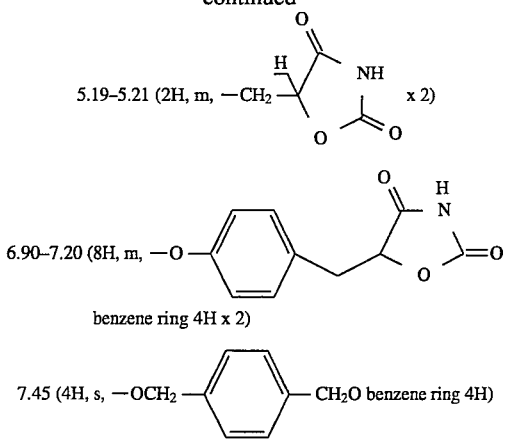

1,4-bis[[4-[(3-trityl-2,4-dioxo-5-oxazolidinyl)methyl]phenoxy]methyl]cyclohexane.

The oily material thus obtained was dissolved in 30 ml of trifluoroacetic acid, allowed to stand still for 1 hour at room temperature, evaporated to dryness under a reduced pressure and then subjected to silica gel column chromatography (hexane-tetrahydrofuran (1:1)) to obtain trans-1,4-bis[[4-[(2,4-dioxo-5-oxazolidinyl)methyl]phenoxy]methyl]cyclohexane. Physicochemical properties of this compound coincided with those of the aforementioned compound of Example 19-c.

TABLE 1

| Example No. | Chemical Formula |
|---|---|
| 1 | (1-a) |
| " | (1-b) |
| 2 | |
| 3 | |

Example 25

To 6.8 g of 3-trityl-2,4-oxazolidinedione dissolved in 200 ml of tetrahydrofuran were added 13.6 ml of n-butyllithium and, after 15 minutes of stirring at −78° C., 3.9 g of trans-1,4-bis[(4-chloromethylphenoxy)methyl]cyclohexane which has been dissolved in 20 ml of tetrahydrofuran, followed by additional 2 hours of stirring at −78° C. After completion of the reaction, the reaction mixture was dispersed in saturated ammonium chloride aqueous solution and ice layers and extracted with ethyl acetate. The ethyl acetate layer was washed with saturated sodium chloride aqueous solution, dried over anhydrous sodium sulfate and then evaporated to dryness, thereby obtaining crude trans-

TABLE 2

| Example No. | Chemical Formula |
|---|---|
| 4 | |
| 5 | |
| 6 | |
| 7 | |

TABLE 3

| Example No. | Chemical Formula |
|---|---|
| 8 | |
| 9 | |
| 10 | |
| 11 | |

TABLE 4

| Example No. | Chemical Formula |
|---|---|
| 12 | (structure: thiazolidinedione-CH₂-C₆H₄-OCH₂-C₆H₄-CH₂O-C₆H₄-CH₂-thiazolidinedione) |
| 13 | (structure: thiazolidinedione-CH₂-C₆H₄-OCH₂-C₆H₄(meta)-CH₂O-C₆H₄-CH₂-thiazolidinedione) |
| 14 | (structure: thiazolidinedione-CH₂-C₆H₄-OCH₂-C₆H₄(ortho)-CH₂O-C₆H₄-CH₂-thiazolidinedione) |
| 15 | (15-a) (structure with bicyclic ether core bearing two aryl-O substituents linked to ylidene-thiazolidinediones) |
|  | (15-b) (structure with bicyclic ether core bearing two aryl-O substituents linked via CH₂ to thiazolidinediones) |

TABLE 5
| Example No. | Chemical Formula |
|---|---|
| 16 | |
| 17 | |
| 18 | (18-a) |
| " | (18-b) |
45
TABLE 6
| Example No. | Chemical Formula |
|---|---|
| 19 | (19-b) |
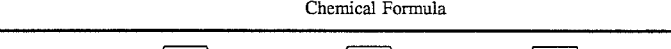

TABLE 6-continued
| Example No. | Chemical Formula |
|---|---|
| " | 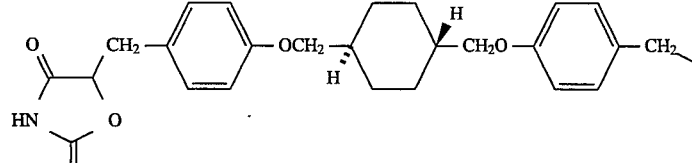<br>(19-c) |
| 20 | 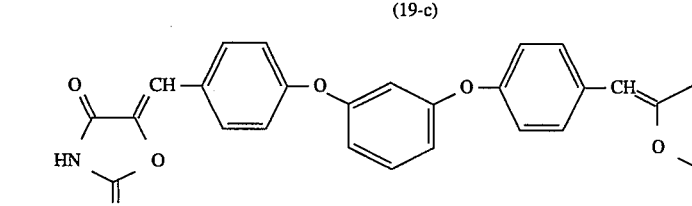<br>(20-b) |
| " | 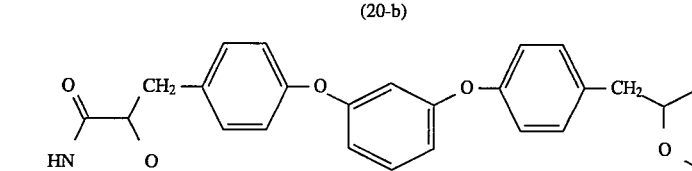<br>(20-c) |
TABLE 7
| Example No. | Chemical Formula |
|---|---|
| 21 | 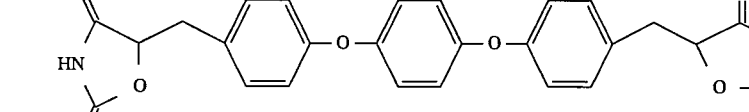 |
| 22 | 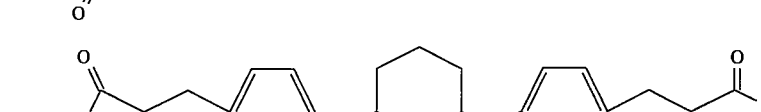 |
| 23 | 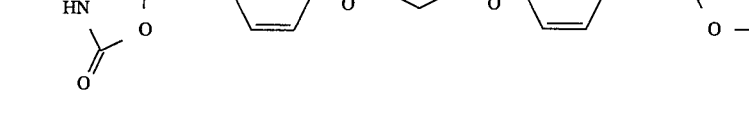 |

TABLE 7-continued

| Example No. | Chemical Formula |
|---|---|
| 24 | |

(full-row structure shown in image)

We claim:

1. A bisheterocyclic compound represented by the following general formula (I)

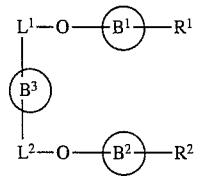

wherein $R^1$ and $R^2$ may be the same or different from each other and each represents a group of the formula:

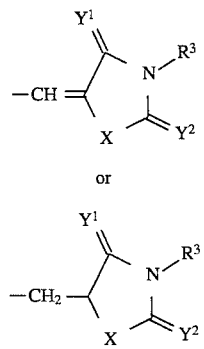

wherein $R^3$ represents a hydrogen atom or a protective group, X, $Y^1$ and $Y^2$ may be the same or different from one another and each represents an oxygen atom or a sulfur atom, $B^1$ and $B^2$ each represents a phenylene group or a naphthylene group $B^3$ represents a phenylene group, a naphthylene group, a cyclohexylene group or a furo[3,2-b] furanylene group, $L^1$ and $L^2$ each represents a group represented by the formula $-(O)_n-A-$, n represents an integer of 0 or 1, and A represents a single bond or a lower alkylene group, provided that when n is 1, A represents a lower alkylene group and the oxygen atom of each of $L^1$ and $L^2$ is bonded to or a stereoisomer thereof, a tautomer thereof, a pharmaceutically acceptable salt thereof or a pharmaceutically acceptable solvate thereof.

2. The compound according to claim 1, wherein $B^3$ is a phenylene group or a cyclohexylene group.

3. The compound according to claim 1, wherein $R^1$ and $R^2$ may be the same or different from each other and each represents a group of the formula:

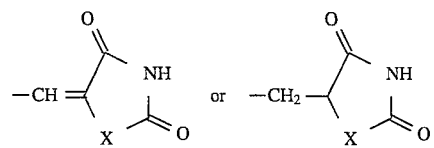

(wherein X has the same meaning as described above).

4. The compound according to claim 1, wherein each of $R^1$ and $R^2$ is a group represented by the formula:

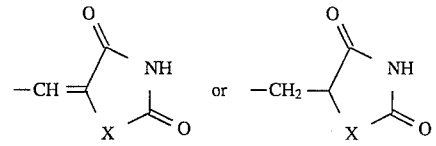

(wherein X has the same meaning as described above) and $B^3$ is a phenylene group or a cyclohexylene group.

5. The compound according to claim 1, wherein said compound is from the group consisting of:
trans-1,4-bis[[4-[(2,4-dioxo-5-thiazolidinyl)methyl]phenoxy]methyl]cyclohexane,
trans-1,4-bis[[4-[(2,4-dioxo-5-oxazolidinylidene)methyl]phenoxy]methyl]cyclohexane,
trans-1,4-bis[[4-[(2,4-dioxo-5-oxazolidinyl)methyl]phenoxy]methyl]cyclohexane,
1,3-bis[4-[(2,4-dioxo-5-oxazolidinyl)methyl]phenoxy]benzene,
1,3-bis[4-[(2,4-dioxo-5-oxazolidinylidene)methyl]phenoxy]benzene,
1,3-bis[4-[(2,4-dioxo-5-oxazolidinyl)methyl]phenoxy]cyclohexane, and
1,3-bis[4-[(2,4-dioxo-5-thiazolidinyl)methyl]phenoxy]cyclohexane.

6. A pharmaceutical composition which comprises a bisheterocyclic compound represented by the following formula (I)

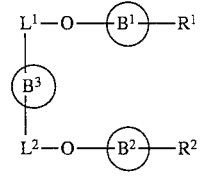

wherein $R^1$ and $R^2$ may be the same or different from each other and each represents a group of the formula:

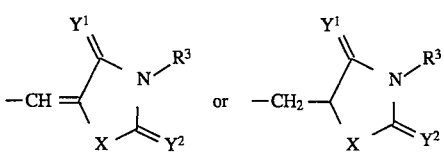

wherein R³ represents a hydrogen atom, X, Y¹ and Y² may be the same or different from one another and each represents an oxygen atom or a sulfur atom, B¹ and B² each represents a phenylene group, B³ represents a phenylene group, a naphthylene group, a cyclohexylene group or a furo[3,2-b]furanylene group, L¹ and L² each represents a group represented by the formula —(O)ₙ—A—, wherein n represents an integer of 0 or 1, and A represents a single bond or a lower alkylene group, provided that when n is 1, A represents a lower alkylene group and the oxygen atom of each of L¹ and L² is bonded to B³, or a stereoisomer thereof, a tautomer thereof, a pharmaceutically acceptable salt thereof, and a pharmaceutically acceptable carrier.

7. A method for enhancing insulin sensitivity in a patent which comprises administering to said patient an insulin sensitivity enhancing amount of the pharmaceutical composition of claim 6.

8. The method of claim 7 wherein the bisheterocyclic compound is present in daily dose amount of from 10 to 2000 mg.

9. The method of claim 7 wherein the bisheterocyclic compound is selected from the group consisting of:
trans-1,4-bis[[4-[(2,4-dioxo-5-thiazolidinyl)methyl]phenoxy]methyl]cyclohexane,
trans-1,4-bis[[4-[(2,4-dioxo-5-oxazolidinylidene)methyl] phenoxy]methyl]cyclohexane,
trans-1,4-bis[[4-[(2,4-dioxo-5-oxazolidinyl)methyl]phenoxy]methyl]cyclohexane,
1,3-bis[4-[(2,4-dioxo-5-oxazolidinyl)methyl]phenoxy]benzene,
1,3-bis[4-[(2,4-dioxo-5oxazolidinylidene)methyl]phenoxy] benzene,
1,3-bis[4-[(2,4-dioxo-5-oxazolidinyl)methyl]phenoxy]cyclohexane and
1,3-bis[4-[(2,4-dioxo-5-thiazolidinyl)methyl]phenoxy]cyclohexane.

* * * * *